United States Patent [19]

Yamaguchi et al.

[11] 4,263,656
[45] Apr. 21, 1981

[54] VISUAL SIGHTING SYSTEM

[75] Inventors: Takao Yamaguchi; Yutaka Ohara, both of Tokyo, Japan

[73] Assignee: Hiroyasu Funakubo, Tokyo, Japan

[21] Appl. No.: 13,276

[22] Filed: Feb. 21, 1979

[30] Foreign Application Priority Data

Sep. 4, 1978 [JP] Japan ................................. 53/108373

[51] Int. Cl.³ .......................... A61F 1/00; G06F 15/20
[52] U.S. Cl. ......................................... 364/559; 3/1.1; 364/413
[58] Field of Search ................ 364/559, 413; 3/1, 1.1, 3/12, 12.8; 414/4, 5

[56] References Cited

U.S. PATENT DOCUMENTS

3,769,636  11/1973  Friedman .................................. 3/1.1
4,030,141   6/1977  Graupe ..................................... 3/1.1

Primary Examiner—Edward J. Wise
Attorney, Agent, or Firm—Blanchard, Flynn, Thiel, Boutell & Tanis

[57] ABSTRACT

A visual sighting system, in which the attitude of a person's head facing to a target object is detected, and the position of the target object is calculated so that an external servomechanism, such as an artificial arm, is directed to the target object.

5 Claims, 15 Drawing Figures

VISUAL SIGHTING SYSTEM

BACKGROUND OF THE INVENTION

This invention relates to a visual sighting system for directing a servomechanism, particularly an artificial limb.

In operating an artificial limb, it is required that the operator can easily communicate with the artificial limb physically and mentally. However, there has not been developed any artificial limb directing system which satisfies these conditions.

SUMMARY OF THE INVENTION

The present invention proposes a visual sighting system basing on the natural movement of a person's head which unconsciously rotates and inclines to bring a target object into sight when the person looks at the target object, wherein the visual sighting system comprises direction sensors which detect the rotation of a person's head around its vertical axis by sensing the terrestrial magnetism; inclinometers which detect the inclination of the person's head with respect to the horizontal plane; and data processing circuits which calculate angular coordinate values of a target object in order to direct an external servomechanism.

DETAILED DESCRIPTION OF THE PREFERRED EMBODIMENT

Figure 13:
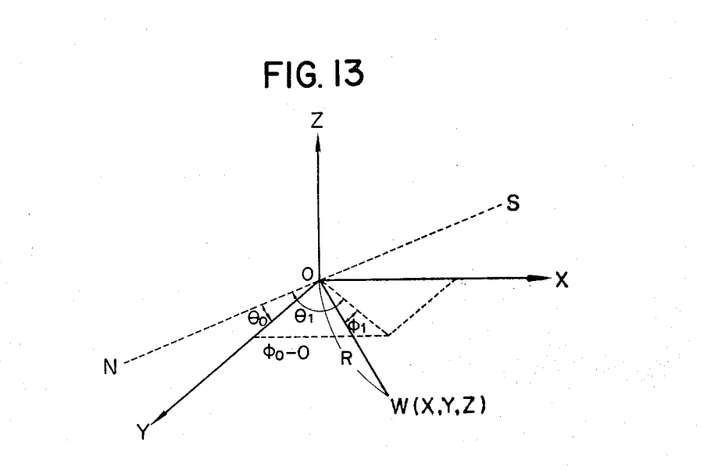
FIG. 13 is an illustration defining physical values in the specification.

The principle of the visual sighting system according to the present invention will initially be explained referring to FIG. 13, where line N-S indicates the direction of terrestrial magnetism, X-Y-Z are angular coordinates where X and Y axes define the horizontal plane, and Z axis defines the vertical plane. The coordinates are initially established so that the standard sight direction O-Y is placed with an initial sight angle $\theta$· apart from the line N-S.

The operator's eyes at the origin O look at a target object located at point W with a distance R from the origin with a horizontal sight angle $\theta$ from the line N-S, and a vertical sight angle $\phi$ from the horizontal plane.

Since the horizontal component of the terrestrial magnetism is used to calculate the position of a target object a direction sensor output (cos $\theta$) is modified using the following equation.

$$F_H = (Ml - F \sin I \cdot \sin \phi)/\cos \phi \quad (1)$$

wherein $F_H$: Horizontal component of the terrestrial magnetism $F$: Total terrestrial magnetism $Ml$: Sensor output (cos $\theta$)

$I$: Dip

When the operator looks at the target object located at point W (x,y,z) using both eyes, values X, Y, and Z can be expressed in the following equations:

$$\left. \begin{array}{l} X = R \cos \phi_1 \cdot \sin(\theta_1 - \theta_0) \\ Y = R \cos \phi_1 \cdot \cos(\theta_1 - \theta_0) \\ Z = R \sin \phi_1 \end{array} \right\} \quad (2)$$

wherein R is distance between O and W, and can be given as:

$$R = a/(\cos \phi \cdot \sin(\theta_1 - \theta_2)) \quad (3)$$

where a is the distance between centres of the operator's eyes, and $\theta_2$ is a horizontal sight angle measured from the line N-S when the operator looks at the target object with one eye. The following operations are performed to evaluate the above equations:

(1) Establishing a standard sight direction to obtain an initial sight angle $\theta$·.
(2) Sighting a target object with both eyes to obtain a first horizontal sight angle $\theta_1$ and a vertical sight angle $\phi_1$.
(3) Sighting the same target object with one eye to obtain a second horizontal sight angle $\theta_2$.

When a standard sight direction O-Y is once determined and fixed, positions of other target objects can be calculated by repeating the above operations (2) and (3).

Next, when an artificial arm is directed to move to the target object, the height of the target object can be calculated using the following equation if the length and a current vertical angle of the artificial arm are known.

$$ZH = (L_1 \sin \alpha + L_2 \sin \beta) \quad (4)$$

where $L_1$: Length of the upper section of artificial arm.
$L_2$: Length of the lower section of artificial arm.
$\alpha$: Vertical angle of the upper section of artificial arm.
$\beta$: Vertical angle of the lower section of artificial arm.

Since distance R can be obtained using the third equation of (2) if height z and a vertical sight angle $\phi_1$ are known, values X and Y can also be obtained using the remaining equations of (2). In this case, the following operations are performed to evaluate the above equations:

(1) Establishing a standard sight direction to obtain an initial sight angle $\theta$·.
(2) Positioning the artificial arm to the target object to obtain a height ZH.
(3) Sighting the target object with both eyes to obtain a horizontal angle $\theta_1$ and a vertical angle $\phi_1$.

When a standard sight direction is once determined and fixed, positions of other target objects at a constant height can be calculated only by repeating the above operation (3).

Thus, positions of several target objects are calculated repeatedly and transmitted to the artificial arm control system, so that the artificial arm moves following the sighted target objects, from point to point.

Another feature of the preferred visual sighting system according to this invention is to identify 17 kinds of sectional areas on a target pattern, so that 17 signals corresponding to the sectional target areas can be switched as a substitution of 17 key switches, issuing commands to an external control system. The following Table shows an example of commands, by which six electric motors are switched to operate.

| Motor   |         | M1 | M2 | M3 | M4 | M5 | M6   |
|---------|---------|----|----|----|----|----|------|
| Command | STOP    | 0  | 3  | 6  | 9  | C  | F    |
|         | NORMAL  | 1  | 4  | 7  | A  | D  | BASE |
|         | REVERSE | 2  | 5  | 8  | B  | E  | —    |

Figure 14:
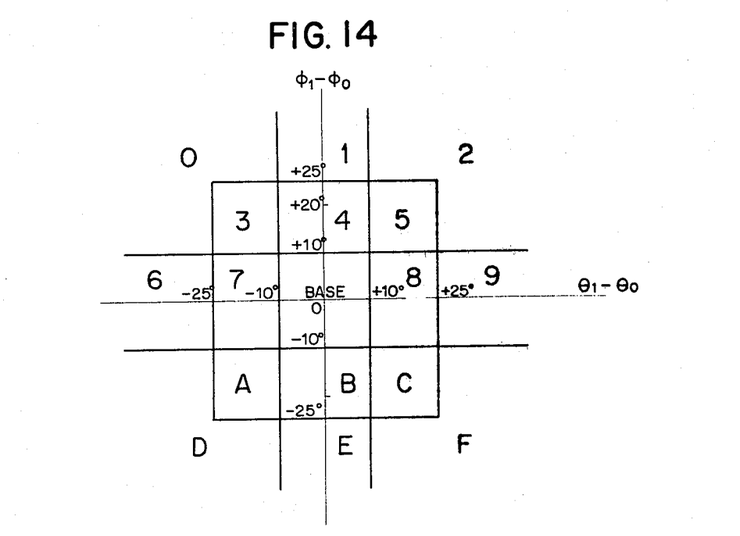
FIG. 14 is an illustration of a target pattern.

FIG. 14 shows a target pattern with 17 sectional target areas to produce 17 command signals.

Figure 15:
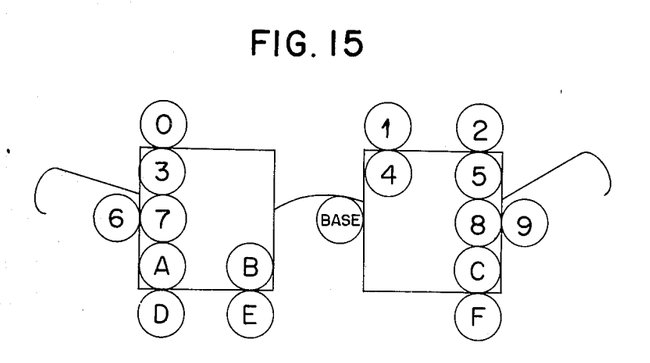
FIG. 15 is an illustration of a display unit.

FIG. 15 shows a display unit of the spectacles type for visually acknowledging the 17 kinds of command signals. On the display unit, 17 photodiodes are attached, each photodiode being located correspondingly to each sectional target area shown FIG. 14.

Figure 1:
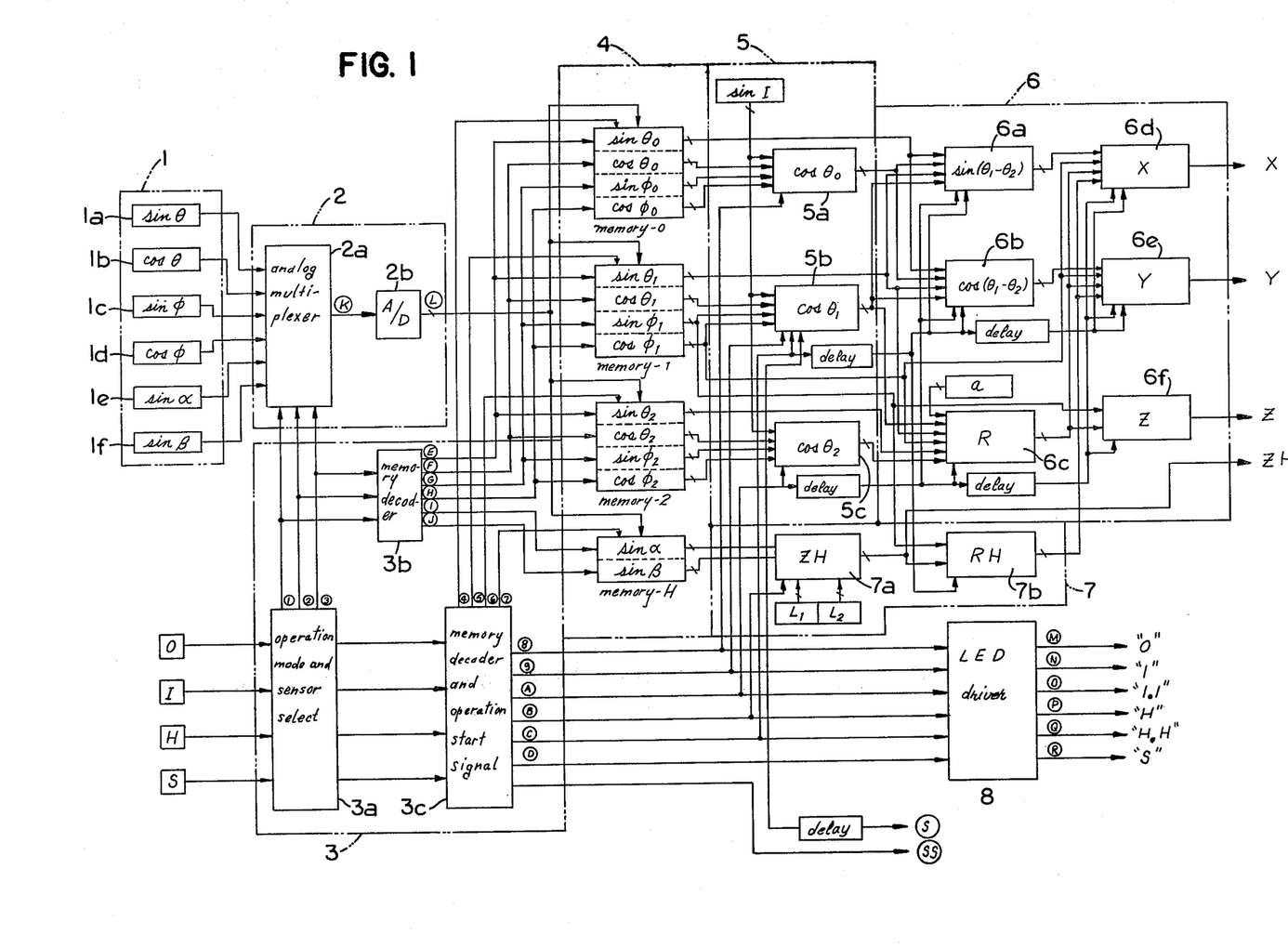
FIGS. 1 and 2 are schematic circuit diagrams of a preferred embodiment of the invention.

The invention will now be further described referring to the schematic circuit diagrams. In FIG. 1, sensor section 1 comprises a pair of direction sensors 1a and 1b which detect the rotation of person's head around its vertical axis, and inclinometers 1c through 1f of the moving magnet torque balancing type detecting the inclination of the person's head. The direction sensors 1a and 1b are attached to the person's head, being placed in right angle against each other, and they detect an angle $\theta$ between a sighting direction and the terrestrial magnetism in the functions $\sin \theta$ and $\cos \theta$, respectively.

A pair of inclinometers 1c and 1d are attached to a person's head, detecting inclination angle $\phi$ of the direction sensors with respect to the horizontal axis as the functions $\sin \phi$ and $\cos \phi$, respectively.

Inclinometers 1e and 1f are attached to the artificial arm, detecting angle $\alpha$ and $\beta$ of the artificial arm upper and lower sections with respect to the horizontal plane, as the functions $\sin \alpha$ and $\sin \beta$.

Input control section 2 comprises an input multiplexer 2a which selects input signals from the sensor section 1, and an A/D converter 2b which converts an analog signal to a digital signal.

Data control section 3 comprises a multiplexer controller 3a which generates selecting signals for the input multiplexer 2a, memory addresser 3b which produces address signals for memory section 4 where input signals are stored, and operation controller 3c which gates the memory input and produces operation signals 8, 9, A, B, C, and D.

The memory section 4 comprises four memory blocks, memory-0, memory-1, memory-2, and memory-H.

Data modification section 5 includes calculators 5a, 5b, and 5c which modify input data obtained through the direction sensors.

Position calculating section 6 includes calculators 6a and 6b which evaluate the sine and cosine functions, and calculators 6c, 6d, 6e, and 6f which calculate distance R and angular coordinate values X, Y, and Z, respectively.

Height calculating section 7 is used to obtain positions of several target objects whose height are constant, comprising calculator 7a which calculates a height ZH of a target object using input data $\sin \alpha$ and $\sin \beta$, and calculator 7b which calculates a distance RH (which is equivalent to distance R) using the calculated data ZH.

Display section 8 amplifies the operation signals from the operation controller 3c to display process modes 0, 1, 1.1, H, H.H, and S.

Figure 2:
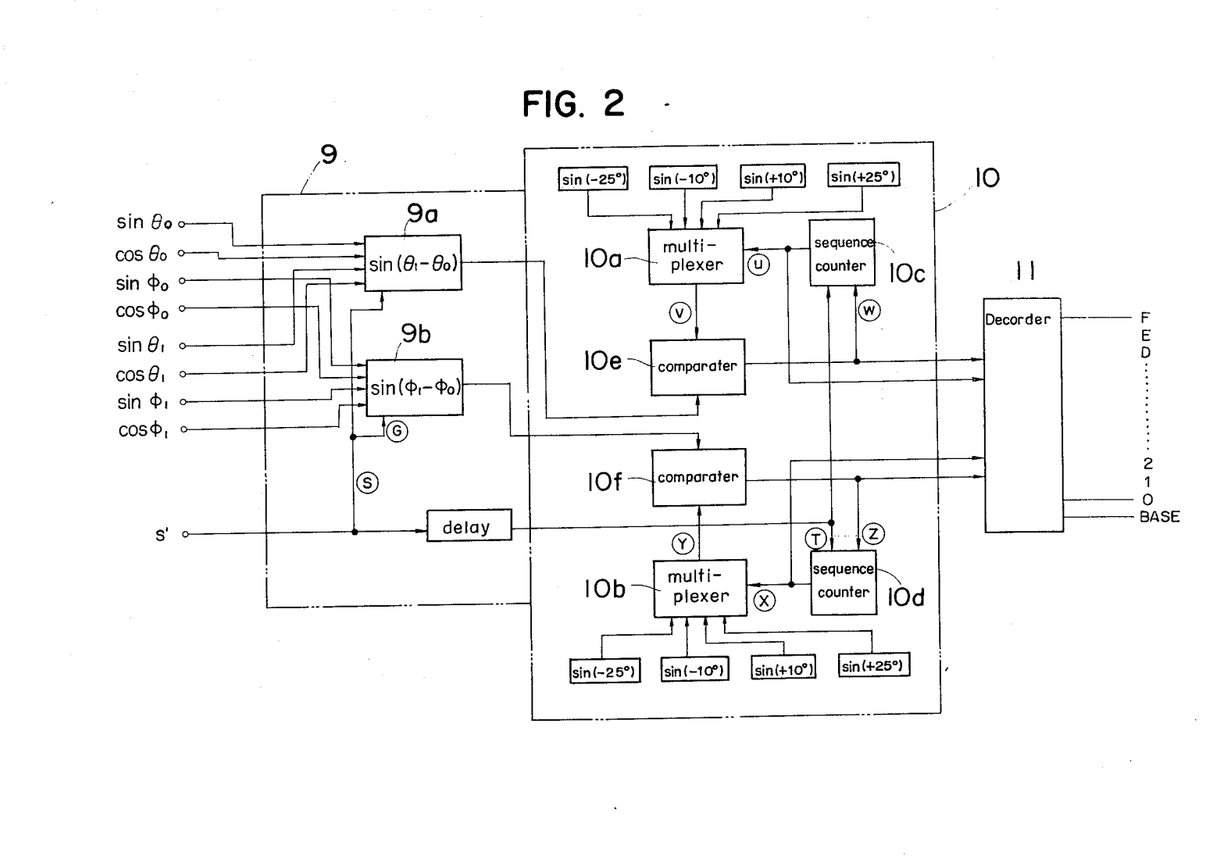

In FIG. 2, direction calculating section 9 includes calculators 9a and 9b which evaluates the sine function using data stored in the memory section 4 and modified data from the data modification section 5.

Direction discrimination section 10 includes multiplexers 10a and 10b which select horizontal and vertical boundary values respectively, sequence counters 10c and 10d which generate selecting signals for the multiplexers, and comparators 10e and 10f which compare data from the calculators 9a and 9b with the horizontal and vertical boundary values, respectively.

Decoder section 11 outputs 17 signals according to the sight identified direction.

Figure 4:
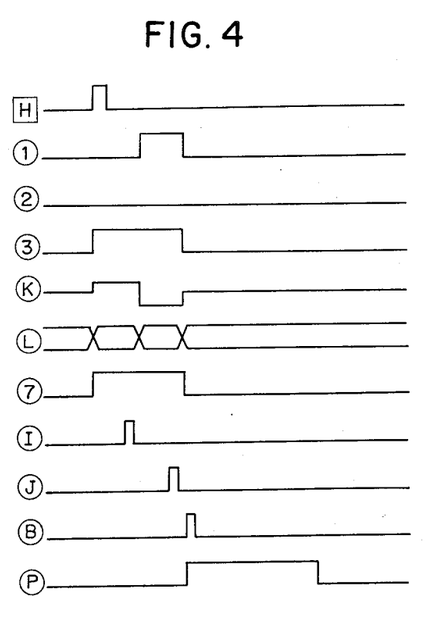
Figure 5:
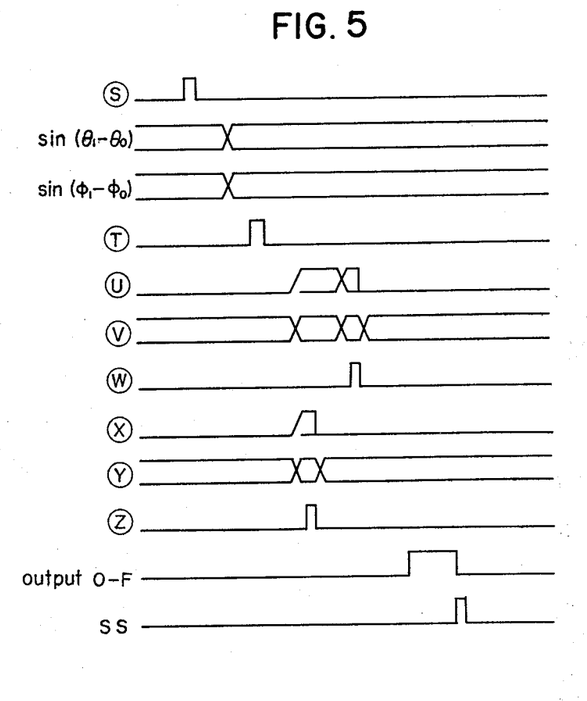

Operation of the preferred visual sighting system will now be explained referring to the timing diagrams (FIG. 3 to FIG. 5) and the flow diagrams (FIG. 6 to FIG. 12) together with the schematic circuit diagrams (FIG. 1 and FIG. 2).

Figure 3:
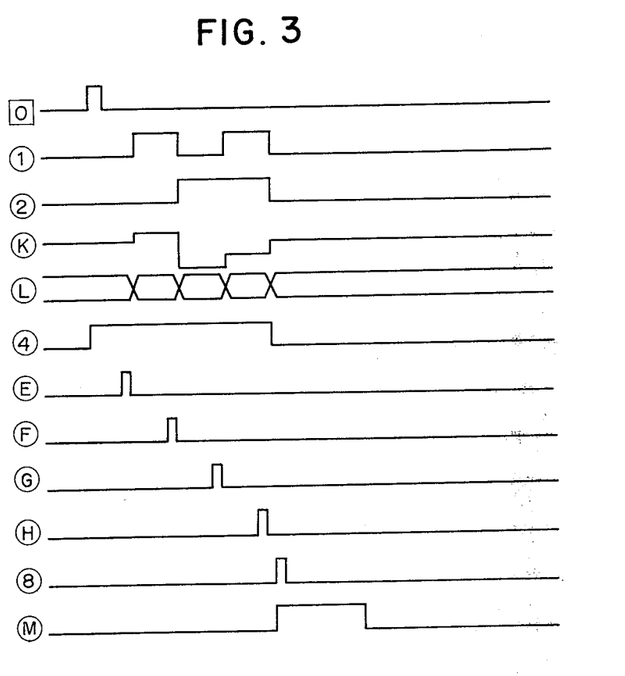
FIGS. 3, 4 and 5 are timing diagrams showing some important signals in the circuit diagrams.

In FIG. 3, when command ⓞ is input to the multiplexer controller 3a, the system is initialized to have process mode O, and multiplexer control signals ① and ② are generated. (See also FIG. 1 and FIG. 6.) The input multiplexer 2a samples input signals $\sin \theta°$, $\cos \theta°$, $\sin \theta°$, and $\cos \theta°$, sequentially, and outputs a serial analog signal Ⓚ. The signal Ⓚ is converted into a serial digital signal Ⓛ in the A/D converter 2b.

Memory selecting signal 4 is produced in the operation controller 3c correspondingly to command ⓞ, so that memory-O in the memory section 4 is selected. The memory addresser 3b produces address signals Ⓔ, Ⓕ, Ⓖ, and Ⓗ sequentially from the signals ① and ②, so that the serial digital signal Ⓛ is memorized in the memory-O.

Figure 7:
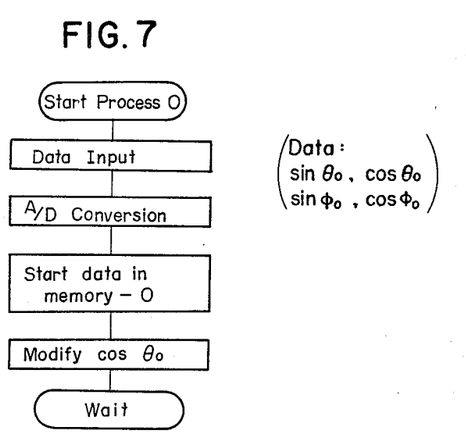
FIGS. 7 to 12 are flow diagrams explaining the operation sectionally in detail.

When all input data (which have been in the form of a serial digital signal) are stored in individual sections of the memory-O, operation signal ⑧ is emitted from the operation controller 3c, and calculation for modifying the input data $\cos \theta°$ according to the equation (1) is executed. FIG. 7 shows a flow diagram explaining the above processing in the process mode O.

Figure 6:
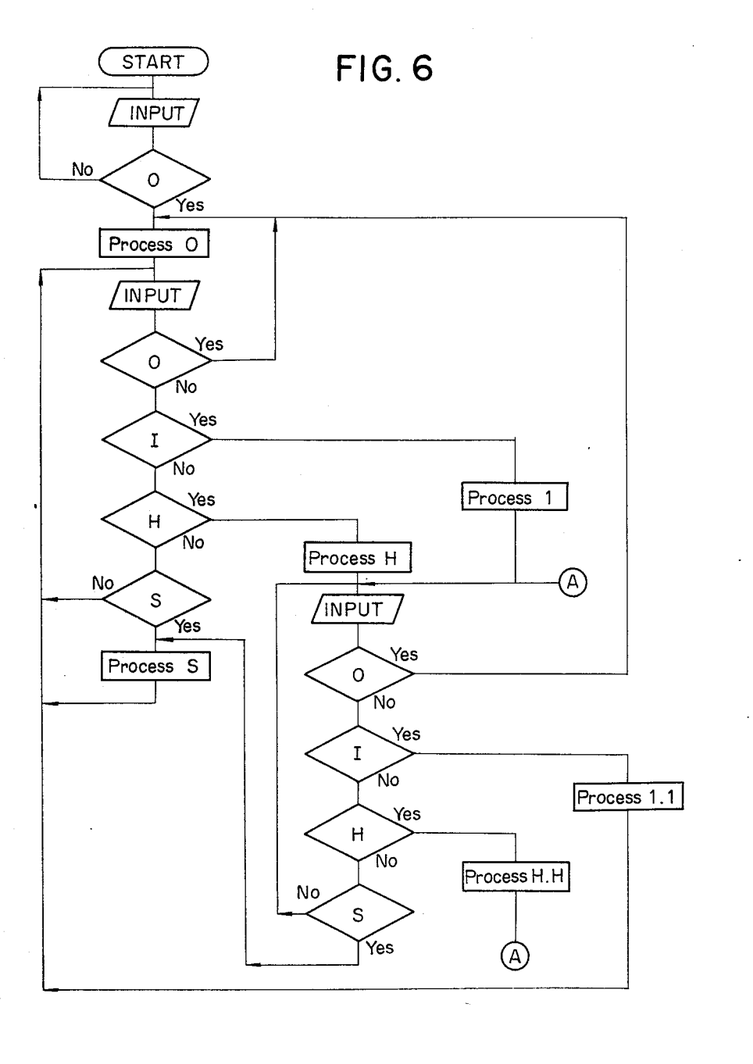
FIG. 6 is a flow diagram explaining overall operation of the circuit diagrams.
Figure 8:
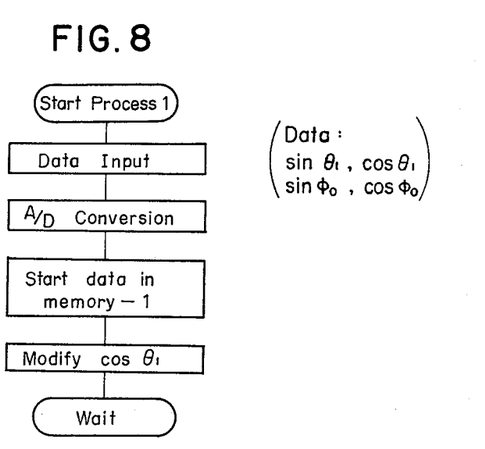

In FIG. 6, the control enters "WAIT" status when the process O is completed. When command ① is given for calculating the position of a target object, the process mode turns to 1, and input signals $\sin \theta_1$, $\cos \theta_1$, $\sin \phi_1$, and $\cos \phi_1$ are sampled and stored in memory-1 in the same manner as in the case of the process O, except for signal ⑤ emitted from the operation controller 3c instead of signal ④ in the previous process mode. Data of $\cos \theta_1$ is modified in calculator 5b following signal ⑨ emitted from the operation controller 3c. FIG. 8 shows a flow diagram explaining the above processing in the process mode 1.

Returning to FIG. 6, the control enters "WAIT" status when the process 1 is completed. When command ① is given again, the process mode turns to 1.1, and input signals $\sin \theta_2$, $\cos \theta_2$, $\sin \phi_2$, and $\cos \phi_2$ are sampled and stored in memory-2 in the same manner as in the case of the process mode 1, except for signal ⑥ emitted from the operation controller 3c, instead of signal ⑤ in the previous process mode. Data of $\cos \theta_2$ is modified in calculator 5c, following operation signal Ⓐ emitted from the operation controller 3c.

Figure 9:
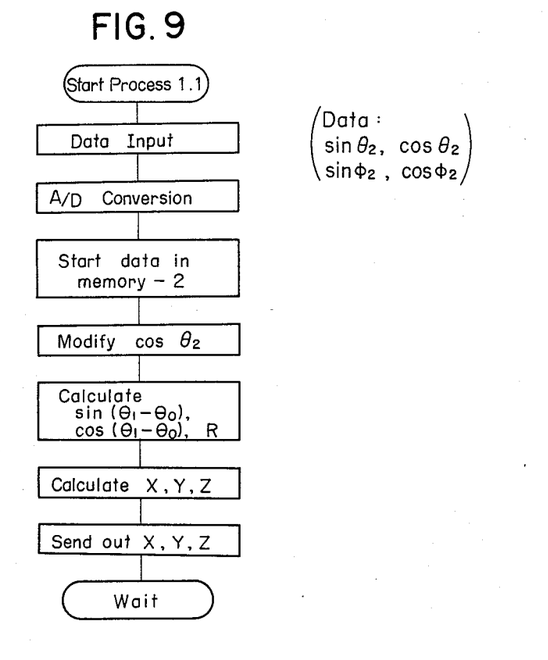

After a certain delay time, in which data for $\cos \theta_2$ is modified, calculators 6a, 6b and 6c are activated so that the functions $\sin (\theta_1 - \theta°)$, $\cos (\theta_1 - \theta°)$ and R in equations (2) and (3) are evaluated. After another delay time, calculators 6d, 6e and 6f are activated so that equations (2) are calculated. Calculated values X, Y and Z are sent out to the external artificial arm control system for directions the arm to the target object. FIG. 9 shows a flow diagram explaining the above processing in the process mode ⑪.

Figure 10:
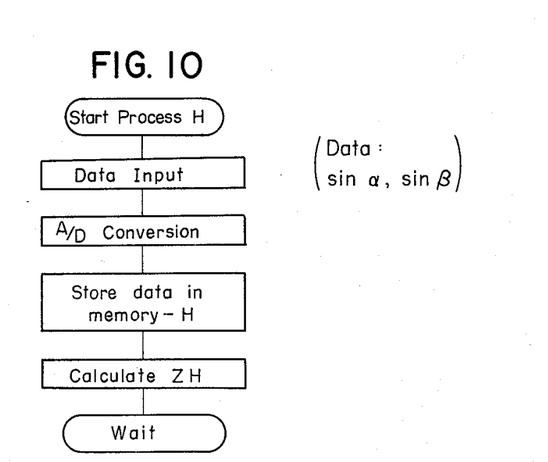

In FIG. 6, when command Ⓗ is given following the process 11, in order to calculate a height ZH of the target object using data turns to H, memory select and address signals ⑦, Ⓘ and Ⓙ are generated, and input signals sin α and sin β are sampled and stored in memory-H. When input data are stored, signal Ⓑ is emitted to activate calculator 7a so that equation (3) is calculated. FIG. 10 shows a flow diagram explaining the above processing in the process mode H.

Again in FIG. 6, the control enters "WAIT" status on completion of the process H. When command Ⓗ is given again, the process mode turns to H.H, and input signals sin $\theta_1$, cos $\theta_1$, sin $\phi_1$, and cos $\phi_1$ are sampled and stored in memory-1. Then, operation signal Ⓒ is emitted to modify data cos $\theta_1$.

Figure 11:
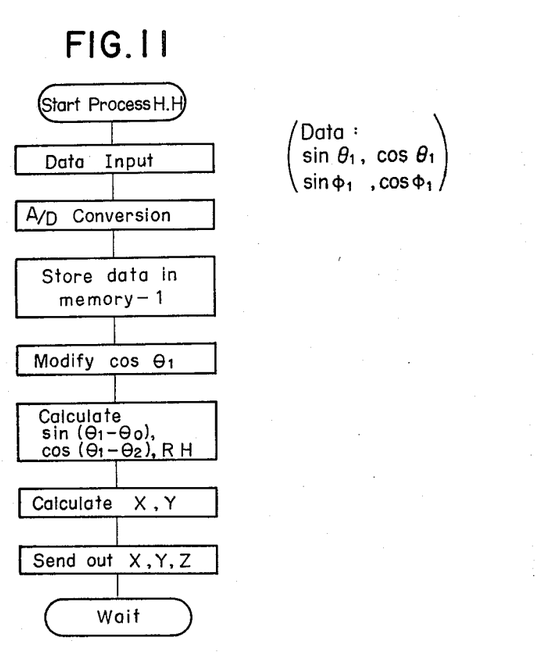

After a certain delay time, calculators 6a, 6b and 7b are activated so that the functions sin $(\theta_1-\theta\cdot)$, cos $(\theta_1-\theta\cdot)$ and RH $(=ZH/\sin \phi_1)$ are evaluated. After another delay time, calculators 6d, 6e are activated so that equations (2) for X and Y, in which RH is used as R at this time, are calculated. Then, values X and Y are sent out to the external artificial arm control system together with a constant height ZH for directing the arm to the target object. FIG. 11 shows a flow diagram explaining the above processing in the process mode H.H.

Finally, when command Ⓢ is given, input signals sin $\theta_1$, cos $\theta_1$, sin $\phi_1$, and cos $\phi_1$ are sampled and stored in the memory-1 in the same manner as described previously. Operation signal Ⓓ is emitted to modify the data $\theta_1$, and after a certain delay time, calculators 9a and 9b are activated by signal Ⓢ, so that the functions sin $(\theta_1-\theta\cdot)$ and sin $(\phi_1-\phi\cdot)$ are evaluated. After another delay time following the signal Ⓢ, signal Ⓣ is produced, and sequence counters 10c and 10d are started.

Boundary values for sectional target areas on a target pattern are provided as sin $(-25°)$, sin $(-10°)$, sin $(10°)$ and sin $(25°)$ for each horizontal and vertical sight angle, and these values are selected sequentially in multiplexers 10a and 10b which are controlled by the sequence counter 10c and 10d, respectively.

Data of sight angles from calculators 9a and 9b are compared with each boundary value sequentially beginning with sin $(-25°)$ in comparator 10e and 10f, respectively, and when the input data is discriminated to be smaller than a boundary value, the corresponding sequence counter is stopped. When both sequence counters stop, contents of the sequence counters are decoded into 17 output signals in decoder section 11, and of these output signals "0" through "9", "A" through "F" and "BASE" is sent out to a corresponding photodiode on the display unit shown in FIG. 15 for acknowledging the sighted target area.

Figure 12:
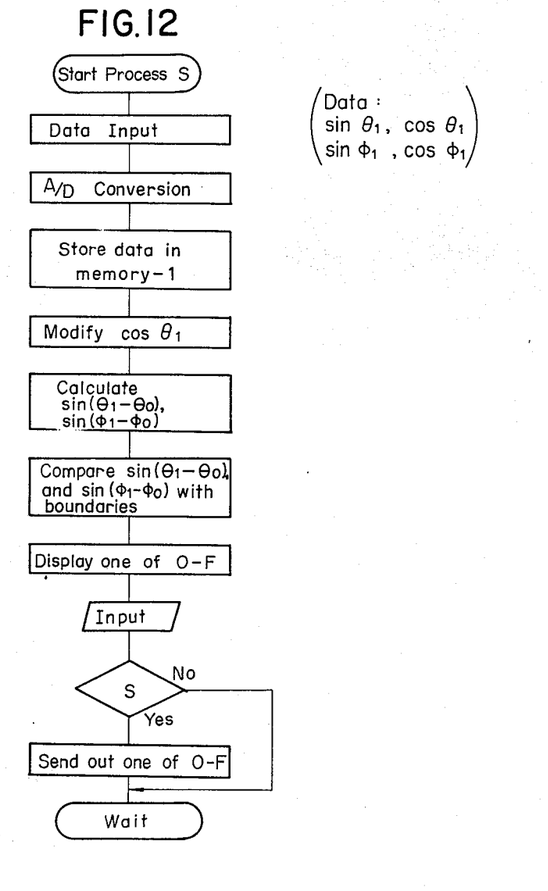

When a correct sighting is acknowledged, command Ⓢ is again given, and the output signal is sent out to the external control system to be used for commanding. FIG. 12 shows a flow diagram explaining the above processing in the process mode S.

Although the system according to the present invention is used in combination with the mechanism of artificial arms in the above embodiment, it can be used for artificial limb including artificial legs.

As this invention may be embodied in several forms without departing from the spirit of essential characteristics thereof, the present embodiment is therefore illustrative and not restrictive, since the scope of the invention is defined by the apended claims rather than by the description preceding them, and all changes that fall within meets and bounds of the claims, or equivalence of such meets and bounds are therefore intended to embraced by the claims.

What is claimed is:

1. A method of detecting a target object position, comprising:
   a first step including setting an attitude of an attitude detecting means, which incorporates a direction sensor and an inclinometer attached on a person's head, against a target object in space, detecting in a horizontal plane by means of said direction sensor an angle $\theta$ between a line which connects said attitude detecting means and said target object and a line of force of the terrestrial magnetism, and detecting in a vertical plane an angle $\phi$ between the line which connects the attitude detecting means and the target object and a line vertical to a horizontal plane; and
   a second step of calculating from said detected angles $\theta$ and $\phi$ a positional relationship between said attitude detecting means and said target object relative to a positional relationship between said attitude detecting means and a predetermined reference target object.

2. A method of detecting a target object position using an attitude detecting means including a direction sensor and an inclinometer attached to a person's head, comprising:
   a first step comprising
   setting the attitude of said attitude detecting means against a reference target object;
   detecting in a horizontal plane an angle $\theta\cdot$ between a line which connects said attitude detecting means to said reference target object and a line of terrestrial magnetic force;
   detecting in a vertical plane an angle $\phi\cdot$ between a line which connects said attitude detecting means to said reference target object and a line vertical to a horizontal plane;
   setting the attitude of said attitude detecting means against a target object;
   detecting in a horizontal plane an angle $\theta_1$ between a line which connects said attitude detecting means to said target object and the line of force of the terrestrial magnetism; and
   detecting in a vertical plane an angle $\phi_1$ between a line which connects said attitude detecting means to said target object and a line vertical to a horizontal plane; and
   a second step comprising
   calculating the difference between said $\theta\cdot$ and $\theta_1$, and the difference between said $\phi\cdot$ and $\phi_1$; and
   generating an electrical signal corresponding to said differences $(\theta_1-\theta\cdot)$ and $(\phi_1-\phi\cdot)$.

3. A method of detecting a target object position using an attitude detecting means including a direction sensor and an inclinometer attached to a person's head, comprising:
   a first step comprising setting the attitude of said attitude detecting means such that a reference target object is located on a perpendicular bisector of two points at both eyes of said person, and detecting in a horizontal plane an angle $\theta°$ between a line which connects said attitude detecting means to said reference target object and a line of force of the terrestrial magnetism;

setting the attitude of said attitude detecting means such that a target object is located on a perpendicular bisector of two points at both eyes of said person, and detecting in a horizontal plane an angle $\theta_1$ between a line which connects said attitude detecting means to said target object and the line of force, and detecting in a vertical plane an angle $\phi_1$ between a line which connects said attitude detecting means to said target object and a line vertical to a horizontal plane;

setting the attitude of said attitude detecting means such that said target object is located on a line which is perpendicular to a line connecting two points at both eyes of said person and which passes through a point at one eye of said person, and detecting in a horizontal plane an angle $\theta_2$ between a line which connects said attitude detecting means to said target object and the line of force; and a second step comprising calculating a distance R between said attitude detecting means and said target object according to an equation $R = a/(\cos \theta \cdot \sin (\theta_1 - \theta°))$ where a is a distance between the centers of a person's eyes;

calculating a component Y of said R along a line (Y axis) connecting said attitude detecting means to said reference target object according to an equation $Y = R \cdot \cos \phi \cdot \sin (\theta_1 - \theta°)$;

calculating a component X of said R along a line which is perpendicular to said Y axis in a horizontal plane according to an equation $X = R \cdot \cos \phi \cdot \sin (\theta_1 - \theta°)$; and calculating a vertical component Z of said R according to an equation $Z = R \cdot \sin \phi$.

4. A visual sighting system for detecting a target object which a person is looking at and including an attitude detector, comprising:

means including first and second direction sensors arranged at a right angle to each other and attached to a person's head for detecting in a horizontal plane an angle $\theta$ between a line which connects said attitude detector and a line of force of terrestrial magnetism and thereby for sensing rotation of said person's head around its vertical axis;

means including first and second inclinometers attached to said person's head for detecting in a vertical plane an angle $\phi$ between the line which connects the attitude detector and target object and a line vertical to the horizontal plane, and thereby sensing the inclination of said person's head with respect to the horizontal plane, said first and second direction sensors providing signals representing the functions $\sin \theta$ and $\cos \theta$, respectively, said first and second inclinometers providing signals representing the functions $\sin \phi$ and $\cos \phi$, respectively.

5. The apparatus of claim 4 including means including third and fourth inclinometers, securable on upper and lower sections of an artificial limb which is to be guided to follow said target object, for detecting the vertical angle $\alpha$ of the upper section of said limb and the vertical angle $\beta$ of the lower section of said arm.

* * * * *